(12) United States Patent
Schwieker

(10) Patent No.: US 7,641,391 B2
(45) Date of Patent: Jan. 5, 2010

(54) CEILING MOUNT FOR X-RAY SYSTEM

(75) Inventor: Horst-Hartwig Schwieker, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 248 days.

(21) Appl. No.: 10/598,259

(22) PCT Filed: Feb. 25, 2005

(86) PCT No.: PCT/IB2005/050697

§ 371 (c)(1),
(2), (4) Date: Aug. 23, 2006

(87) PCT Pub. No.: WO2005/087105

PCT Pub. Date: Sep. 22, 2005

(65) Prior Publication Data

US 2007/0140435 A1 Jun. 21, 2007

(30) Foreign Application Priority Data

Mar. 8, 2004 (EP) .................................. 04100935

(51) Int. Cl.
*H05G 1/02* (2006.01)
(52) U.S. Cl. ..................................................... 378/197
(58) Field of Classification Search .......... 378/193–198
See application file for complete search history.

(56) References Cited

U.S. PATENT DOCUMENTS

| | | | | |
|---|---|---|---|---|
| 4,435,830 A | * | 3/1984 | Suzuki et al. | 378/197 |
| 6,155,713 A | | 12/2000 | Watanabe | 378/197 |
| 2003/0091151 A1 | | 5/2003 | Horbaschek et al. | 378/196 |

FOREIGN PATENT DOCUMENTS

| | | |
|---|---|---|
| DE | 2747583 A | 4/1979 |
| WO | WO03021629 A | 3/2003 |

* cited by examiner

*Primary Examiner*—Courtney Thomas

(57) ABSTRACT

The invention relates to an X-ray installation having two ceiling mounts (20, 30), to which the X-ray tube (26) respectively the X-ray detector (36) are fixed. The ceiling mounts comprise crossbeams (21, 31), which are mounted on the guide rails (11, 12) so as to slide in the longitudinal direction ($L_s$, $L_D$) and which in turn carry carriages (22, 32) slidable in the transverse direction ($T_s$, $T_D$). Length-adjustable arms (23, 33) are secured to the carriages (22, 23) and at their ends are mounted transverse arms (24, 34) rotatable about a vertical axis of rotation ($R_{1S}$, $R_{1D}$). The transverse arms in turn carry equipment carriers (25, 35) rotatable about axes of rotation ($R_{2S}$, $R_{2D}$), to which lastly the X-ray tube (26) respectively the X-ray detector (36) are secured.

18 Claims, 1 Drawing Sheet

CEILING MOUNT FOR X-RAY SYSTEM

Figure 1:
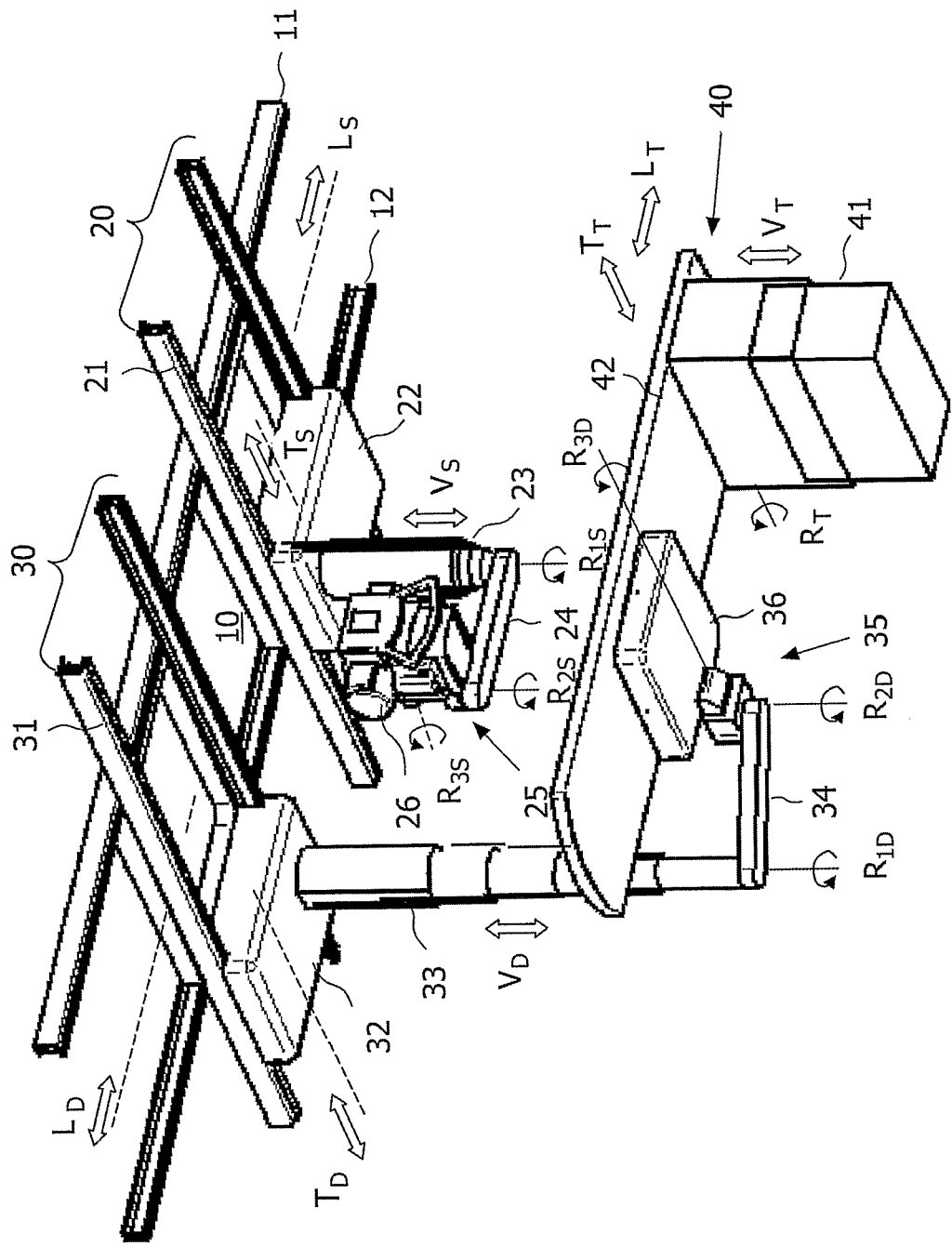

The invention relates to a ceiling mount for an X-ray tube or an X-ray detector, and to an X-ray installation having two such ceiling mounts.

DE 27 47 583 A1 discloses an X-ray installation in which the X-ray tube (X-ray source) and the X-ray detector are each mounted on ceiling mounts. With this arrangement, first of all a rotary frame is fixed below the ceiling of an examination room so as to be rotatable about a vertical axis. Two guide rails are disposed on the rotary frame, on which two crossbeams are linearly displaceable independently of one another. To the crossbeams in turn there are affixed slidable arms, the length of which can be adjusted in the vertical direction. The X-ray tube and X-ray detector are then mounted at a respective lower end of the arms so as to pivot about a horizontal axis of rotation.

Against this background it was an object of the present invention to provide a ceiling mount for an X-ray installation that permits optimum utilization of space and can be realized with comparatively little effort involved in mounting.

The ceiling mount according to the present application can support an X-ray tube or alternatively an X-ray detector. It contains the following components:

a) A first guide arrangement, which can be fixed to the ceiling of an examination room. Typically, this guide arrangement comprises two or more parallel rails, on which equipment can be mounted so as to slide linearly.
b) A carrier system, comprising a length-adjustable arm, the carrier system being mounted on the above-mentioned first guide arrangement so as to slide in a first direction. Typically, the first direction is a horizontal direction, which in an examination room extends parallel to the lengthwise direction of a patient table. In that case, the carrier system can therefore be displaced along the longitudinal axis of a patient lying on the patient table. In a manner known from DE 27 47 583 A1, for example, the arm is formed from two or more segments so that its length is alterable. In the mounted state of the ceiling mount, the longitudinal or extension axis of the arm extends preferably in the vertical direction, so that with a length alteration the height of the equipment being carried can be adjusted.
c) A transverse arm, which is mounted at the free end of the above-mentioned arm so as to be rotatable about a first axis of rotation. The transverse arm can comprise one piece, or alternatively a plurality of segments joined by hinges.
d) An equipment carrier, which is mounted at the free end of the above-mentioned transverse arm so as to be rotatable about a second axis of rotation, and which carries the X-ray tube or the X-ray detector.

The ceiling mount described permits a wide range of settings for an X-ray tube or X-ray detector, combined with a comparatively simple and stable construction. At the same time, the first guide arrangement and the arm allow, for example, position variability in a lengthwise direction and in a vertical direction. The transverse arm and the equipment carrier moreover allow the position of the mounted equipment to be changed on the spot in the remaining degrees of freedom. Of particular advantage in this connection is the fact that, by virtue of the transverse arm, the final position of the mounted equipment does not have to lie vertically beneath the mounting point of the arm, so that the latter is able to extend vertically downwards from the ceiling at a different place where it interferes less.

According to a further aspect of the ceiling mount, the carrier system mentioned under b) comprises the following two components:

b1) a second guide arrangement, which is mounted on the first guide arrangement so as to slide in the first direction, and
b2) a carriage, which is mounted on said second guide arrangement so as to slide in a second direction and which carries the arm. Preferably, the second direction and the first direction are perpendicular to one another. Furthermore, both directions can lie in a horizontal plane, the first direction corresponding typically to a longitudinal axis and the second direction corresponding typically to a transverse axis in relation to a patient table.

By providing a second guide arrangement within the carrier system, the arm is rendered freely positionable in a second direction independent of the first direction. In this way, the origin of the arm can be positioned virtually as desired on the ceiling.

The extension axis of the arm is preferably perpendicular to the first direction in which the carrier system is slidably mounted on the first guide arrangement. If the carrier system is constructed in two parts, as described above, with a carriage slidable in a second direction, the extension axis of the arm is preferably moreover also perpendicular to that second direction. If the first and the second directions are horizontal and perpendicular to one another, the three degrees of freedom (first and second direction, extension axis) enable the end point of the arm to be freely positionable at virtually any desired point in space.

The first axis of rotation, about which the transverse arm is pivotally mounted at the end of the arm, can in principle be any desired axis. Preferably, however, it extends parallel to the extension axis of the arm. If the arm is of rotationally symmetrical construction about its extension axis, the first axis of rotation is preferably identical with the centerline or axis of symmetry of the arm. With the described arrangement of the first axis of rotation, the free end point of the transverse arm describes a circular arc around the arm. The maximum reach of the transverse arm is thereby achieved. The transverse arm extends preferably perpendicularly to the extension axis of the arm, so that it projects radially from the arm.

The spatial orientation of the second axis of rotation about which the equipment system is pivotable relative to the end of the transverse arm can in principle be as desired. Preferably, however, the second axis of rotation extends parallel to the first axis of rotation, about which the transverse arm fixed to the end of the arm is rotatable. As already mentioned, the first and the second axes of rotation can run in particular parallel to the extension axis of the arm and/or vertically. Parallelism of the first and second axes of rotation has the advantage that the spatial orientation of the equipment carrier can be kept constant in a simple manner, if, upon each rotation of the transverse arm about the first axis of rotation, a rotation of the equipment carrier about the second axis of rotation is performed through an inverse angle of the same size.

According to a preferred further aspect of the ceiling mount, the equipment mounted thereon, (that is, the X-ray tube or the X-ray detector) is secured to the equipment carrier so as to be rotatable about a third axis of rotation. This provides further freedom in respect of the choice of projection direction of the X-ray system. The third axis of rotation can in particular lie perpendicular to the second axis of rotation (about which the equipment carrier at the end of the transverse arm is able to rotate), so that rotations independent of one another can be performed about both axes.

The present application relates furthermore to an X-ray installation, in which the X-ray tube is secured to a first ceiling mount and the X-ray detector is secured to a second ceiling mount. Here, as described above, the ceiling mounts each contain the following components:

a) a first guide arrangement, which can be fixed to the ceiling of a room;
b) a carrier system, having a length-adjustable arm, the carrier system being mounted on the first guide arrangement so as to slide in a first direction;
c) a transverse arm, which is mounted at the end of the arm so as to be rotatable about a first axis of rotation;
d) an equipment carrier, which is mounted at the end of the transverse arm and which carries the X-ray tube or the X-ray detector.

The X-ray installation is thus characterized by the use of two ceiling mounts of the above-described kind, one for the X-ray tube and one for the X-ray detector. With regard to the properties, advantages and further aspects of the X-ray installation, reference can therefore be made to the above description of the ceiling mounts.

According to a preferred embodiment of the X-ray installation, the ceiling mounts both use the same first guide arrangement. For example, the guide arrangement can comprise two or more parallel rails fixed to the ceiling of an examination room. The shared use of the guide arrangement enables the design of the ceiling mounts to be space-saving or cost-saving.

Moreover, the X-ray installation can contain a patient table, on which a patient to be examined can lie, and which is adjustable in height, in its lengthwise direction, its transverse direction and/or its inclination. Through the co-operation of the two positionable pieces of equipment (tube, detector) and the patient table that can be adjusted in wide ranges, virtually any desired recording configuration between equipment and object can be set.

The X-ray installation is furthermore preferably equipped with an electronic control unit for controlling the spatial set-up (position and orientation) of X-ray tube and X-ray detector. The user then only has to enter specific desired values for the position of the equipment or for the image to be made, and the control unit automatically controls the ceiling mounts so that they take up a favorable configuration, in which the tube and the detector attain their required position. The control unit is furthermore preferably designed so that it allows for collision avoidance, that is, does not initiate any configurations of the ceiling mounts that would cause these to collide with one another.

These and other aspects of the invention are apparent from and will be elucidated with reference to the embodiments described hereinafter.

In the drawings:

The single FIGURE shows in a perspective view from below an X-ray installation according to the invention with two ceiling mounts.

The FIGURE shows only the parts from an X-ray examination room relevant to the present invention. It is a matter here of a first ceiling mount 20, which carries the X-ray tube 26 at its end, and a second ceiling mount 30, which carries the X-ray detector 36 at its end, and the patient table 40, on which a patient to be examined (not illustrated) can lie.

The two ceiling mounts 20, 30 make use of a shared first guide arrangement, which in the example illustrated is formed by two parallel runner rails 11, 12 fixed to the ceiling 10 of the room. Of the ceiling mount 20, a crossbeam 21 is mounted on the rails 11, 12 so as to slide horizontally in a lengthwise direction $L_S$. In particular, the crossbeam 21 may have the form of a rectangular frame, the longer sides of the frame forming runners and being perpendicular to the rails 11, 12 fixed to the ceiling. A carriage 22 is mounted in said runners of the crossbeam 21 so as to slide in a cross-wise or transverse direction $T_S$. As illustrated, the lengthwise direction extends preferably parallel to the lengthwise direction determined by the patient table 40 in the examination room, and the transverse direction extends perpendicular thereto.

A vertically downwardly projecting arm 23 having two or more segments is secured to the carriage 22. By way of example the arm 23 can be designed as a telescoping arm. The arm 23 is adjustable in length by moving its segments apart in a vertical direction $V_S$. A transverse arm 24 is fixed to the lower end of the arm 23 so as to pivot about the vertical longitudinal axis or extension axis $R_{1S}$ of the arm 23. The free end of the transverse arm 24 can thus in principle be positioned on a circular arc around the arm 23.

An equipment carrier 25 is mounted at the end of the transverse arm 24 so as to rotate about a likewise vertical axis of rotation $R_{2S}$. Upon rotation of the transverse arm 24 through a first angle about the first axis of rotation $R_{1S}$, and an opposite rotation of the equipment carrier 25 about the second axis of rotation $R_{2S}$, the spatial orientation of the equipment carrier 25 is thus maintained.

Lastly, the X-ray source 26 is connected to the equipment carrier, and can be pivoted about a third axis of rotation $R_{3S}$, so that the radiation direction of the X-ray tube can be set as desired. Preferably, the third axis of rotation $R_{3S}$ lies perpendicular to the second axis of rotation $R_{2S}$.

The second ceiling mount 30 is in principle of exactly the same construction as the first ceiling mount 20. Merely the dimensioning of individual components, for example, of the arm 33 or of the transverse arm 34 may differ, so that a different area of the room desired for the X-ray detector 36 is accessible in an optimum manner. By way of example the arm 33 can be designed as a telescoping arm. The second ceiling mount 30 is formed by a crossbeam 31, which is mounted on the guide rails 11, 12 so as to slide in the lengthwise direction $L_D$ and which in its turn carries a carriage 32 slidable horizontally in the transverse direction $T_D$. A vertically downwardly projecting arm 33 is mounted on the carriage 32, and at its end is mounted the transverse arm 34 pivotable about the extension axis $R_{1D}$. At its distal end, the preferably horizontally lying transverse arm 34 carries the equipment support 35, which is rotatable about the vertical axis of rotation $R_{2D}$ and on which lastly the X-ray detector 36 pivotable about an axis of rotation $R_{3D}$ is mounted. Here too, the axes $R_{2D}$ and $R_{3D}$ are preferably perpendicular to one another.

Furthermore, the FIGURE shows a patient table 40, which comprises a telescopable stand 41 and fastened thereto a surface 42 for the patient to lie on. The patient table is height-adjustable in the direction of the vertical $V_T$ and slidable in the lengthwise direction $L_T$ and transverse direction $T_T$. Furthermore, it can be inclined about an axis of inclination $R_T$.

The described system with the two ceiling mounts 20, 30 having the shared guide rails 11, 12, combined with optimum utilization of the available space produces an extremely versatile and at the same time stable support system for the X-ray equipment. In particular, this equipment can be used to take lateral radiographs on both sides, tomographs, half-axial radiographs of the skull and the petrous bone. A further advantage is that the horizontal patient is accessible laterally at the level of the X-ray emitter. The transverse arms 24, 34 allow a coverage that permits angle views of the head and a tomography. Furthermore, by virtue of the two vertical axes $R_{1S}$ and $R_{1D}$) a pivoting range of the x-ray tube 26 and the detector 36 respectively beyond the normal transverse travel of the respective carriage 22, 32 is possible. This results in optimum utilization of space. The X-ray system illustrated is further preferably equipped with an electronic motion control and a collision avoidance control, so that the X-ray tube 26 and the X-ray detector 36 can be brought simply and reliably into a desired position in space.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A ceiling mount for an X-ray tube or an X-ray detector, the ceiling mount comprising:
   a) a first guide arrangement that can be fixed to a ceiling of a room;
   b) a carrier system including a depending length-adjustable arm, the carrier system being movably mounted to the first guide arrangement such that it slides in a first direction;
   c) a transverse arm, a first end of which is rotatably mounted to a depending end of the depending adjustable-length arm for rotation about a first axis of rotation;
   d) an equipment carrier, which is rotatably connected with a second end of the transverse arm for rotation about a second axis of rotation, the equipment carrier carrying the X-ray tube or the X-ray detector.

2. The ceiling mount as claimed in claim 1, wherein the equipment carrier is further connected with the second end of the transverse arm for rotation about a third axis of rotation, one of the second axes of rotation and the third axis of rotation being parallel to the first axis of rotation.

3. The ceiling mount as claimed in claim 1, wherein the carrier system comprises:
   b1) a second guide arrangement, which is movably mounted to the first guide arrangement such that the second guide arrangement moves relative to the first guide arrangement in the first direction, and
   b2) a carriage, which is movably mounted to the said second guide arrangement such that the carrier moves in a second direction relative to the second guide arrangement, the second direction being different from the first direction, the carriage carrying the depending length-adjustable arm.

4. The ceiling mount as claimed in claim 1, wherein the first axis of rotation of the depending length-adjustable arm is perpendicular to the first direction.

5. The ceiling mount as claimed in claim 1, wherein the first axis of rotation is parallel to an axis of the depending length-adjustable arm.

6. The ceiling mount as claimed in claim 1, wherein the second axis of rotation is parallel to the first axis of rotation.

7. The ceiling mount as claimed in claim 3, wherein first axis of rotation of the depending length-adjustable arm is perpendicular to the first direction and the second direction.

8. The ceiling mount as claimed in claim 1, wherein the X-ray tube or the X-ray detector is rotatably mounted to the equipment carrier for rotation about a third axis of rotation.

9. The X-ray installation as claimed in claim 5, wherein the X-ray tube and the X-ray are mounted to the first and second equipment carriers for rotation about horizontal axes.

10. A ceiling mount for an X-ray tube or an X-ray detector comprising:
    a) a first guide arrangement that is adapted to be mounted to a ceiling of a room;
    b) a carrier system including, a vertically extending length-adjustable arm, the carrier system being movably mounted to the first guide arrangement such that the carrier system moves along the first guide arrangement,
    c) a transverse arm, a first end of the transverse arm being, rotatably mounted to a free end of the length-adjustable arm for rotation about a first vertical axis of rotation;
    d) an equipment carrier mounted to a second end of the transverse arm, the X-ray tube or the X-ray detector being rotatably connected with the transverse arm via the equipment carrier for rotation about a horizontal axis of rotation.

11. The ceiling mount as claim in claim 10, wherein the equipment carrier is rotatably connected with a second end of the transverse arm for rotation about a second vertical axis.

12. An X-ray installation, wherein an X-ray tube and an X-ray detector are each secured to a ceiling mount, which contains:
    a) a first guide arrangement that can be fixed to a ceiling of a room;
    b) a carrier system having a length-adjustable arm, the carrier system being mounted to the first guide arrangement so that it can slide in a first direction;
    c) a transverse arm, which is mounted to an end of the length-adjustable arm so as to be rotatable about a first axis of rotation;
    d) an equipment carrier, which is mounted to an end of the transverse arm so as to be rotatable about a second axis of rotation and which carries the X-ray tube or the X-ray detector.

13. The X-ray installation as claimed in claim 12, further comprising
    a second carrier system having a second length-adjustable arm, the second carrier system being mounted to the first guide arrangement for movement in the first direction;
    a second transverse arm rotatably mounted to an end of the second length-adjustable arm for rotation about a longitudinal axis of the second length-adjustable arm;
    a second equipment carrier rotatably mounted to an end of the transverse arm for rotation about an axis of rotation which is parallel to the longitudinal axis of the second length-adjustable arm, the other of the X-ray tube and the X-ray detector being carried by the second equipment carrier.

14. The X-ray installation as claimed in claim 12, further including:
    a patient table adjustable in height, lengthwise direction, transverse direction, and/or inclination.

15. The X-ray installation as claimed in claim 13, further including:
    a control unit for controlling spatial adjustments of the X-ray tube and the X-ray detector, making allowances for collision avoidance.

16. The X-ray installation as claimed in claim 13, wherein the first axis of rotation and the second axis of rotation are both vertical.

17. The X-ray installation as claimed in claim 12, wherein the X-ray tube or X-ray detector is mounted to the equipment axis for rotation about a third axis.

18. The X-ray installation as claimed in claim 17, wherein the second and third axes are perpendicular.

* * * * *